US011511124B2

(12) United States Patent
Blecher (10) Patent No.: US 11,511,124 B2
(45) Date of Patent: Nov. 29, 2022

(54) METHOD AND APPARATUS FOR DIRECTING THERAPEUTIC NANOPARTICLE-LABELED CELLS TO SELECTED LOCATIONS WITHIN THE BODY AND/OR FOR RETAINING THERAPEUTIC NANOPARTICLE-LABELED CELLS AT SELECTED LOCATIONS WITHIN THE BODY

(71) Applicant: Sports Medicine Sciences, LLC, Encino, CA (US)

(72) Inventor: Andrew M. Blecher, Encino, CA (US)

(73) Assignee: Sports Medicine Sciences, LLC, Beverly Hills, CA (US)

( * ) Notice: Subject to any disclaimer, the term of this patent is extended or adjusted under 35 U.S.C. 154(b) by 228 days.

(21) Appl. No.: 15/137,286

(22) Filed: Apr. 25, 2016

(65) Prior Publication Data

US 2016/0310078 A1    Oct. 27, 2016

Related U.S. Application Data

(60) Provisional application No. 62/152,546, filed on Apr. 24, 2015.

(51) Int. Cl.
*A61N 2/06* (2006.01)
*A61N 2/00* (2006.01)
(Continued)

(52) U.S. Cl.
CPC .............. *A61N 2/002* (2013.01); *A61K 41/00* (2013.01); *A61K 49/1818* (2013.01); *A61K 49/1896* (2013.01); *A61K 9/0009* (2013.01)

(58) Field of Classification Search
None
See application file for complete search history.

(56) References Cited

U.S. PATENT DOCUMENTS 7,146,651 B1 * 12/2006 Lapin ............... A41D 19/01594
2/338
9,999,380 B1 * 6/2018 Demas ................. H01F 7/0231
(Continued)

OTHER PUBLICATIONS

Kyrtatos et al., "Magnetic Tagging Increases Delivery of Circulating Progenitor in Vascular Injury" JACC: Cardiovascular Interventions, vol. 2, Issue 8. Aug. 2009, pp. 794-802.*
(Continued)

*Primary Examiner* — Colin T. Sakamoto
(74) *Attorney, Agent, or Firm* — Pandiscio & Pandiscio (57) ABSTRACT

A method for directing therapeutic nanoparticle-labeled cells to selected locations within the body and/or for retaining therapeutic nanoparticle-labeled cells at selected locations within the body, the method comprising: providing an article comprising a body of material configured to be secured about the body of a patient and having a plurality of pockets thereon, wherein each pocket is sized to receive and retain one or more magnets therein; injecting therapeutic USPIO nanoparticle-containing cells into a target therapy site; securing the article to the body of the patient; and inserting at least one magnet into at least one pocket so as to provide a desired magnetic field for further directing therapeutic nanoparticle-labelled cells to a target therapy site and/or for retaining therapeutic nanoparticle-labeled cells at the target therapy site.

12 Claims, 7 Drawing Sheets

(51) Int. Cl.
    *A61K 49/18* (2006.01)
    *A61K 41/00* (2020.01)
    *A61K 9/00* (2006.01)

(56) References Cited

U.S. PATENT DOCUMENTS

| | | | |
|---|---|---|---|
| 10,092,452 B2* | 10/2018 | Robinson | A61N 1/40 |
| 2004/0139975 A1* | 7/2004 | Nelson | A61F 2/20 128/848 |
| 2014/0298560 A1* | 10/2014 | Bailey, II | A41D 13/0015 2/69 |

OTHER PUBLICATIONS

Kolosnjaj-Tabi et al., "Cell labeling with magnetic nanoparticles: Opportunity for magnetic cell imaging and cell manipulation" Journal of Nanobiotechnology 2013, 1, (Suppl 1): 57.*
Kim et al., "Synthesis, Characterization, and Application of Ultrasmall Nanoparticles" Chemistry of Materials 2014, 26 (1).*
Costo et al., "Ultrasmall Iron Oxide Nanoparticles for Biomedical Applications: Improving the Colloidal and Magnetic Properties" Langmuir 2012, 28(1), pp. 178-185.*
Kim et al., "Ultrasmall nanoparticles induce ferroptosis in nutrient-deprived cancer cells and suppress tumour growth" Nature Nanotechnology 11, 977-985 (2016).*
Oude Engberink et al., "Comparison of SPIO and USPIO for in vitro labelling of human monocytes with respect to MR detection and cellular activation status" Proc. Intl. Soc. Mag. Reson. Med. 14 (2006).*
Alam et al., "Ultrasmall Superparamagnetic Particles of Iron Oxide in Patients With Acute Myocardial Infarction" Circuilation Cardio-vascular Imaging. (2012) 5:259-565.*
Connell et al., "Advanced cell therapies: targeting, tracking and actuation of cells with magnetic particles" Regen. Med. (2015) 10(6), 757-772 (Year: 2015).*
Arbab et al., "In Vivo Trafficking and Targeted Delivery of Magnetically Labeled Stem Cells" Human Gene Therapy 15:351-360 Apr. 2004 (Year: 2004).*
Children's Hospital of Pittsburgh, UPMC, "Basic MRI Safety".*
Dziedzic et al., "Magnetic Resonance Imaging MRI Safety" Munson Healthcare, Apr. 2008 (Year: 2009).*
Barnagarwala, "Story of an extraordinary death: How MRI machines work, and can (in rare cases) kill", The Indian Express, updated Feb. 7, 2018 (Year: 2018).*
Peck, "Fatal MRI Accident Is First of Its Kind" WebMD Health News, reviewed by Charlotte E. Grayson Mathis, MD, 2001 (Year: 2001).*
ABC News, "Boy, 6, Killed in Freak MRI Accident", Jan. 7, 2006 (Year: 2006).*
"How dangerous are magnetic items near an MRI magnet?" YouTube video published by YouTube username practiCalfMRI on Nov. 12, 2010 (Year: 2010).*
Baghi, Mehran et al., "The Efficacy of MRI with Ultrasmall Superparamagnetic Iron Oxide Particles (USPIO) in Head and Neck Cancers", Anticancer Res. 25(5), Sep.-Oct. 2005, pp. 3665-3670.
Narang, Ajit S. et al. "Targeted Delivery of Small and Macromolecular Drugs", CRC Press, 2010, p. 501.

* cited by examiner

METHOD AND APPARATUS FOR DIRECTING THERAPEUTIC NANOPARTICLE-LABELED CELLS TO SELECTED LOCATIONS WITHIN THE BODY AND/OR FOR RETAINING THERAPEUTIC NANOPARTICLE-LABELED CELLS AT SELECTED LOCATIONS WITHIN THE BODY

REFERENCE TO PENDING PRIOR PATENT APPLICATION

This patent application claims benefit of prior U.S. Provisional Patent Application Ser. No. 62/152,546, filed Apr. 24, 2015 by Andrew M. Blecher for METHOD AND APPARATUS FOR DIRECTING THERAPEUTIC NANOPARTICLE-LABELED CELLS TO SELECTED LOCATIONS WITHIN THE BODY AND/OR FOR RETAINING THERAPEUTIC NANOPARTICLE-LABELED CELLS AT SELECTED LOCATIONS WITHIN THE BODY, which patent application is hereby incorporated herein by reference.

FIELD OF THE INVENTION

This invention relates to methods and apparatus for directing therapeutic cells to selected locations within the body and/or for retaining therapeutic cells at selected locations within the body, and more particularly to methods and apparatus for directing therapeutic nanoparticle-labeled cells to selected locations within the body and/or for retaining therapeutic nanoparticle-labeled cells at selected locations within the body.

BACKGROUND OF THE INVENTION

Companies are now developing ultra-small, superparamagnetic iron oxide (USPIO) nanoparticles which have a coating that enables the nanoparticles to be readily taken up by cells without the aid of transfection agents. Once the USPIO nanoparticles have been taken up by the cells, the USPIO nanoparticles are confined to vacuoles within the cells. The USPIO nanoparticles then effectively "label" the cells. Such labeling does not adversely affect the cells—the cells remain healthy and retain normal function after USPIO nanoparticle labeling.

USPIO nanoparticles can be used as a contrast agent for enhanced magnetic resonance imaging (MRI). In addition, labeled cells (i.e., cells labeled with USPIO nanoparticles) can be created in the laboratory and then introduced into the body for enhanced MRI. Among other things, labeled cells can be created, frozen and stored; after thawing, the cells remain viable and can be introduced into the body while retaining their USPIO nanoparticle labels.

This system has been successfully tested using a wide range of different cell types.

It has been suggested that it is possible to use external magnetic fields to "steer" therapeutic USPIO nanoparticle-containing cells toward a desired site in the body in order to provide therapy to, and/or to enhance imaging of, that site. Thus, the labeled, USPIO nanoparticle-containing cells may be injected into the body and then magnetically steered toward the therapy site.

Unfortunately, such magnetic "steering" of therapeutic USPIO nanoparticle-containing cells is difficult to achieve in practice given the tools currently available and, even where the therapeutic USPIO nanoparticle-containing cells are successfully steered toward the therapy site, it can be difficult to retain the therapeutic USPIO nanoparticle-containing cells at the site, particularly over extended periods of time and/or where the patient is mobile.

SUMMARY OF THE INVENTION

In accordance with the present invention, there is provided a novel method and apparatus for directing therapeutic USPIO nanoparticle-labeled cells to selected locations within the body and/or for retaining therapeutic USPIO nanoparticle-labeled cells at selected locations within the body.

More particularly, and as will hereinafter be discussed in further detail, this is achieved by providing an article (e.g., a sleeve, a wrap, a covering, a brace, etc.) for disposition about an area of the anatomy (e.g., a knee, shoulder, ankle, hip, elbow, hand, spine, thigh, etc.), wherein the article provides a plurality of pockets or compartments or enclosures for receiving magnets which can be used to create a localized magnetic field in order to steer therapeutic USPIO nanoparticle-labeled cells to a therapy site within the body and/or to retain the therapeutic USPIO nanoparticle-labeled cells at that location over extended periods of time and/or while the patient is mobile. For the purposes of the present invention, the terms "pockets" and "compartments" and "enclosures" are intended to have the same meaning and may be used interchangeably.

In one preferred form of the invention, there is provided a method for directing therapeutic nanoparticle-labeled cells to selected locations within the body and/or for retaining therapeutic nanoparticle-labeled cells at selected locations within the body, the method comprising:

providing an article comprising a body of material configured to be secured about the body of a patient and having a plurality of pockets thereon, wherein each pocket is sized to receive and retain one or more magnets therein;

injecting therapeutic USPIO nanoparticle-containing cells into a target therapy site;

securing the article to the body of the patient; and inserting at least one magnet into at least one pocket so as to provide a desired magnetic field for further directing therapeutic nanoparticle-labelled cells to a target therapy site and/or for retaining therapeutic nanoparticle-labeled cells at the target therapy site.

In another preferred form of the invention, there is provided apparatus for directing therapeutic nanoparticle-labeled cells to selected locations within the body and/or for retaining therapeutic nanoparticle-labeled cells at selected locations within the body, the apparatus comprising an article comprising a body of material configured to be secured about the body of a patient, and a plurality of pockets thereon, wherein each pocket is sized to receive and retain one or more magnets therein.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

In accordance with the present invention, there is provided a novel method and apparatus for directing therapeutic USPIO nanoparticle-labeled cells to selected locations within the body and/or for retaining therapeutic USPIO nanoparticle-labeled cells at selected locations within the body.

More particularly, and as will hereinafter be discussed in further detail, this is achieved by providing an article (e.g., a sleeve, a wrap, a covering, a brace, etc.) for disposition about an area of the body (e.g., a knee, shoulder, ankle, hip, elbow, hand, spine, thigh, etc.), wherein the article provides a plurality of pockets or compartments or enclosures for receiving magnets which can be used to create a localized magnetic field in order to steer therapeutic USPIO nanoparticle-labeled cells to a therapy site within the body and/or to retain the therapeutic USPIO nanoparticle-labeled cells at that location over extended periods of time and/or while the patient is mobile. Again, for the purposes of the present invention, the terms "pockets" and "compartments" and "enclosures" are intended to have the same meaning and may be used interchangeably.

By way of example but not limitation, in the field of orthopedics, it is common to provide injectable therapies (e.g., viscosupplementation or regenerative therapies such as platelet rich plasma or stem cell treatment) to selected sites in the body (e.g., the knee, shoulder, ankle, hip, elbow, hand, spine, thigh, etc.). By way of further example but not limitation, in the non-orthopedic field, it is common to provide injectable therapeutic cells for the treatment of tumors, infections, vascular lesions, etc. These therapies provide their therapeutic benefits via the interaction of the injected cells with the cells of the target tissue. However, when the injectable cells fail to reach the target tissue and/or where the injectable cells migrate away from the site of the target tissue (i.e., the therapy site), the injectable cells are no longer able to provide their benefits. Increasing the accuracy with which the injectable cells are delivered to the target site, and/or increasing the "dwell time" that the injectable cells remain at the target site, can improve their therapeutic effects and improve patient outcomes.

Therefore, in accordance with the present invention, the injectable therapeutic cells are labeled with USPIO nanoparticles, and then the USPIO nanoparticle-containing cells are injected into the target therapy site. The USPIO nanoparticle-containing cells may then be further targeted toward the target tissue, and/or better maintained at the location of the target tissue, via a localized, tailored magnetic field. This approach has the potential to improve the clinical outcomes of orthopedic and non-orthopedic therapies that are provided to millions of people worldwide.

In accordance with the present invention, there is provided various articles (e.g., sleeves, wraps, coverings, braces, etc.) that can be placed around various parts of the body such as the knee, shoulder, ankle, hip, elbow, hand, spine, thigh, etc. These articles are configured to receive and hold magnets therein, with the magnets being arranged so as to create the desired magnetic field around the anatomy which is to receive the therapeutic USPIO nanoparticle-labeled cells.

More specifically, the articles (e.g., sleeves, wraps, coverings, braces, etc.) are provided with pockets or compartments or enclosures for receiving the magnets, with the pockets or compartments or enclosures being disposed about the therapeutic site so that appropriate magnets may be positioned in appropriate ones of the pockets or compartments or enclosures so as to create the desired magnetic field about the therapy site, whereby to further direct the USPIO nanoparticle-containing cells to the target tissue and/or to maintain the USPIO nanoparticle-containing cells at the target tissue. It will be appreciated that the magnets may be of different strengths or sizes, and may be deployed at different locations on the article, so as to generate the desired magnetic field about the anatomy (i.e., about the therapy site).

By way of example but not limitation, some of the pockets or compartments or enclosures of the article (e.g., sleeves, wraps, coverings, braces, etc.) may have one or more magnets therein and others of the pockets or compartments or enclosures may have no magnets therein. Where a given pocket or compartment or enclosure has one or more magnets therein, the magnets may all be of one given strength (and/or size), or the magnets may all be of another given strength (and/or size), or the magnets may be a mix of different strengths (and/or sizes).

Thus, the magnetic fields created by placing appropriate magnets in appropriate ones of the pockets or compartments or enclosures of the article (e.g., sleeve, wrap, coverings, brace, etc.) work with the injected therapeutic USPIO nanoparticle-containing cells so as to further direct the therapeutic USPIO nanoparticle-containing cells to the target tissue and/or to maintain the therapeutic USPIO nanoparticle-containing cells at the target tissue, whereby to increase their tissue residency time and therefore improve their therapeutic benefits.

Figure 1:
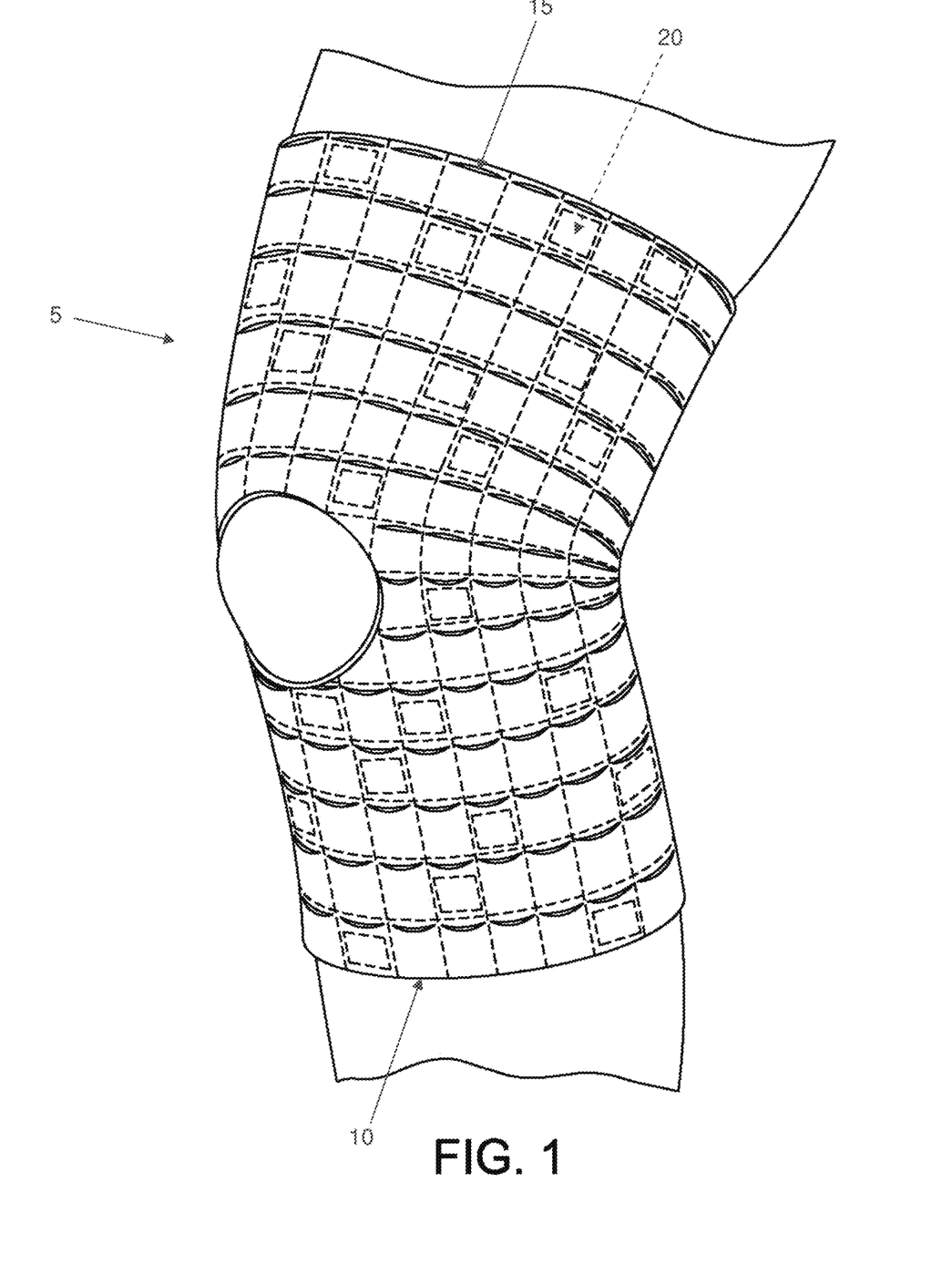
FIGS. 1-3 are schematic views showing a novel article for disposition about the knee of a patient, wherein the novel article is configured to receive magnets which can be used to create a localized magnetic field in order to steer therapeutic USPIO nanoparticle-labeled cells to a therapy site within the body and/or to retain the therapeutic USPIO nanoparticle-labeled cells at that location over extended periods of time and/or while the patient is mobile.
Figure 2:
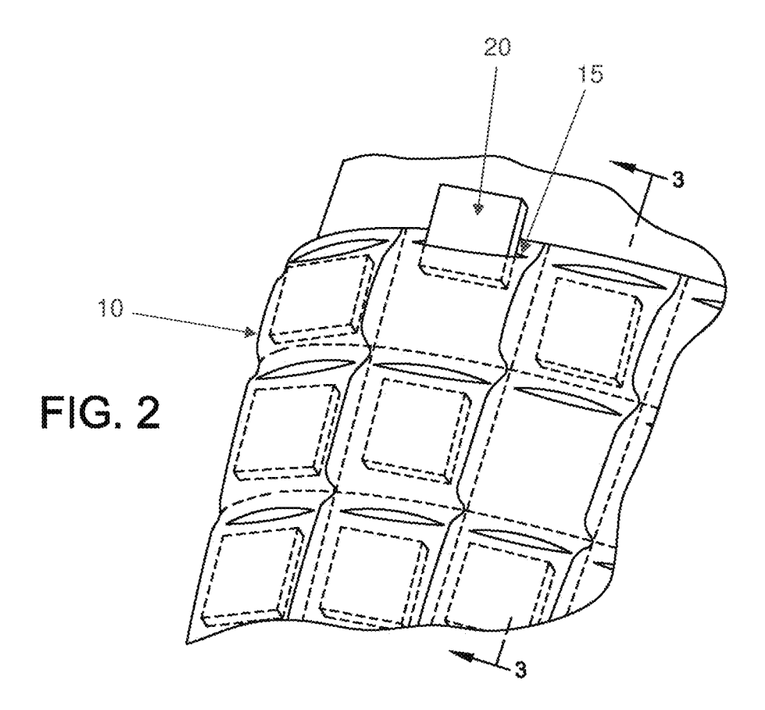
Figure 3:
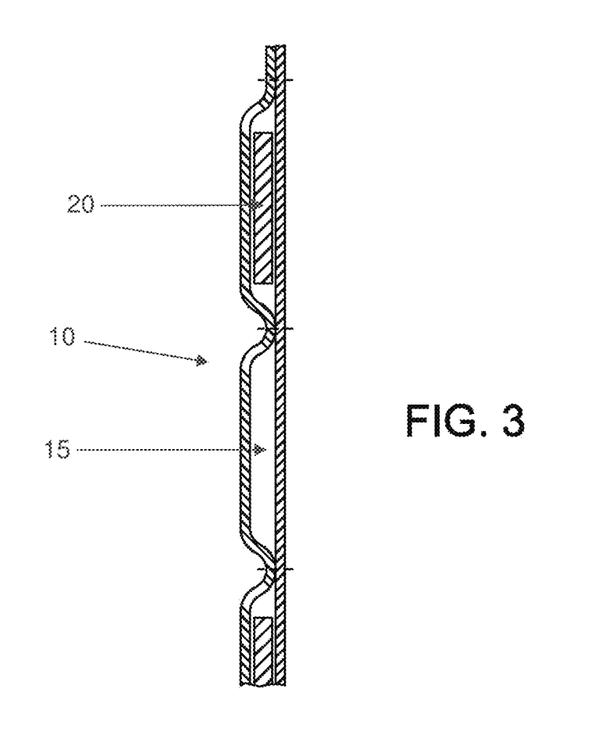

See, for example, FIGS. 1-3, which show an exemplary article 5 (e.g., sleeve, wrap, covering, brace, etc.) for the knee. Article 5 generally comprises a body of material 10 configured to be secured about the knee of the patient, e.g., article 5 may comprise a compression sleeve for making a gripping fit about the knee of the patient. Alternatively, article 5 may comprise a wrap for securement about the knee of the patient. Or article 5 may comprise a brace for securement about the knee of a patient. Or article 5 may comprise another article of the sort well known to those skilled in the art. Note that article 5 may be functional in nature (e.g., to provide a bandage covering, anatomical support, heat retention, etc.) or article 5 may simply serve to support magnets at the appropriate locations about the patient's anatomy.

Article 5 generally comprises a plurality of pockets (or compartments or enclosures) 15 which are each sized to receive and retain one or more magnets 20 therein. By way of example but not limitation, pockets 15 may be generally rectangular, and closed on three sides and open (or openable) on one side, so as to allow one or more magnets to be inserted into (or removed from) a given pocket 15. A closure (e.g., a Velcro fastener) may be provided on the open (or openable) side to allow the pocket to be closed. Pockets 15 may also comprise other (e.g., non-rectangular) shapes if desired. It should be appreciate that pockets 15 may all be of the same shape or pockets 15 may comprise a variety of shapes.

In one preferred form of the invention, pockets 15 are distributed about substantially the entire outer surface of the article and pockets 15 are distributed about article 5 with a regular pattern so as to allow one or more magnets to be disposed at substantially any location on article 5. In another preferred form of the invention, pockets 15 may be distributed at only selected locations about article 5 so as to allow one or more magnets 20 to be disposed at selected locations on article 5.

It should be appreciated that article 5 is configured to be secured to the anatomy of the patient so that the magnets 20 carried by article 5 steer therapeutic USPIO nanoparticle-labeled cells to a desired therapy site within the body, and/or so that the magnets 20 carried by article 5 act to retain the therapeutic USPIO nanoparticle-labeled cells at that location within the body over extended periods of time and/or while the patient is mobile.

Figure 4:
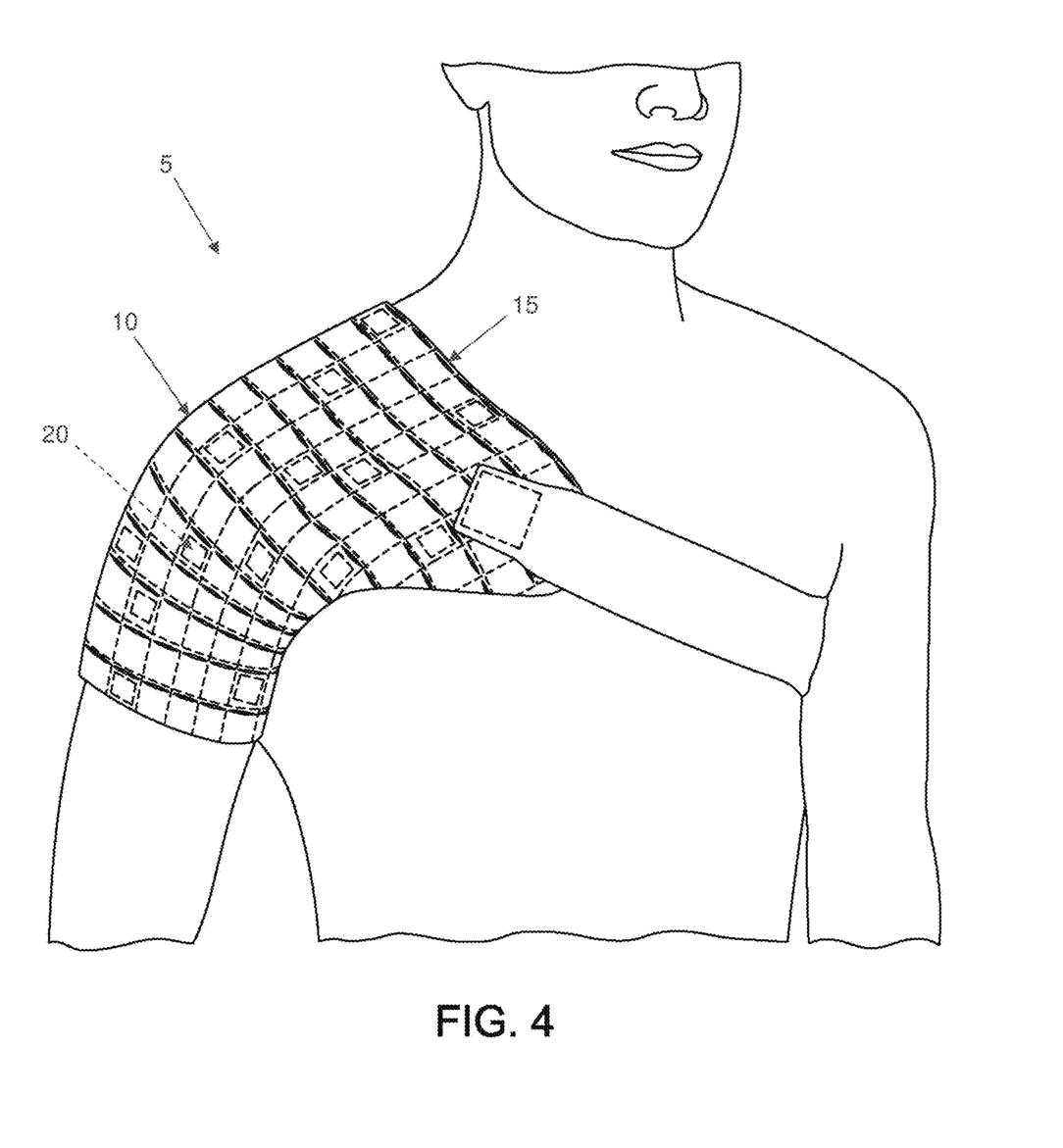
FIG. 4 is a schematic view showing a novel article for disposition about the shoulder of a patient, wherein the novel article is configured to receive magnets which can be used to create a localized magnetic field in order to steer therapeutic USPIO nanoparticle-labeled cells to a therapy site within the body and/or to retain the therapeutic USPIO nanoparticle-labeled cells at that location over extended periods of time and/or while the patient is mobile.

FIG. 4 shows an exemplary article 5 (e.g., a sleeve, wrap, covering, brace, etc.) adapted to be worn on the shoulder of a patient.

Figure 5:
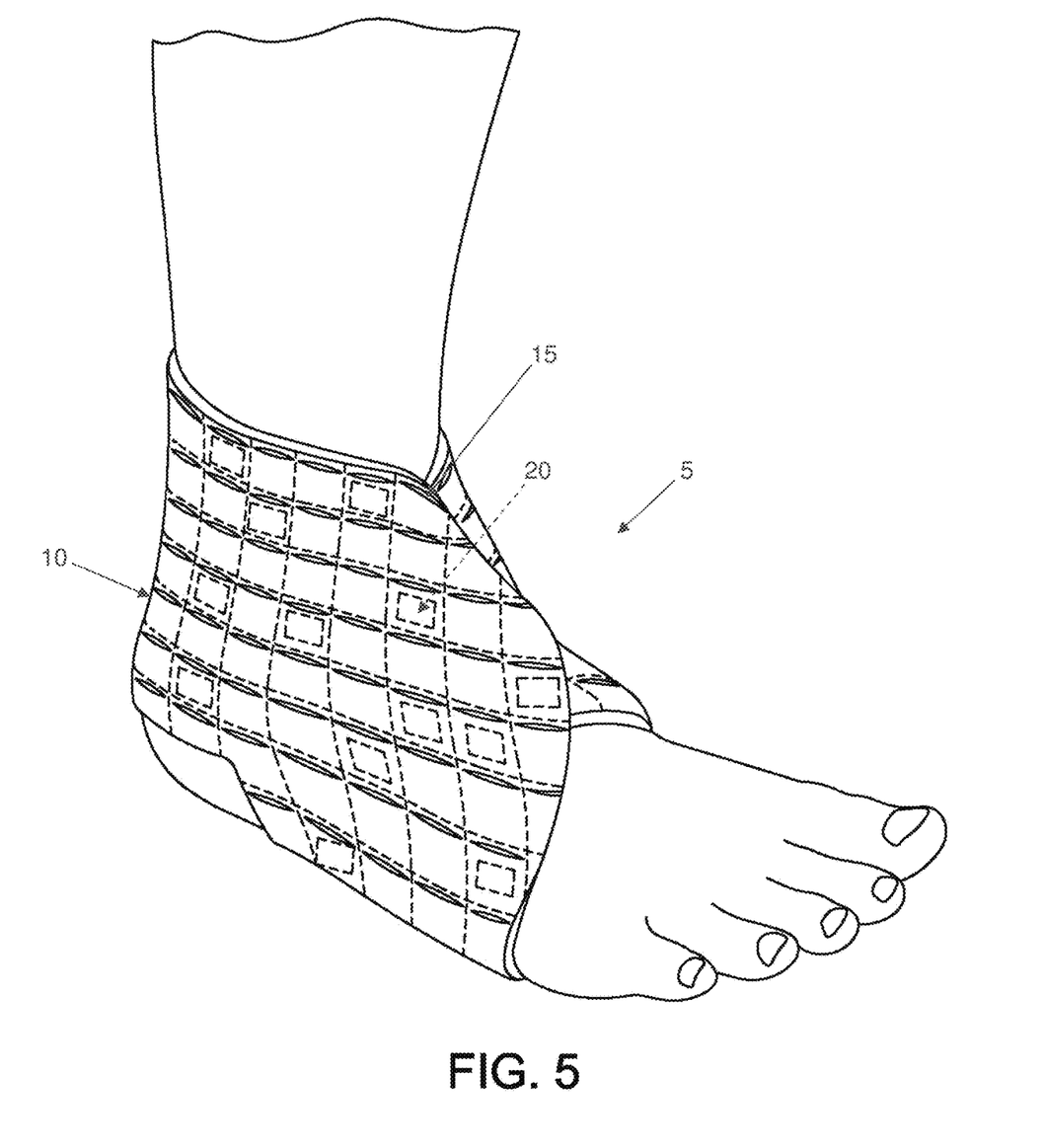
FIG. 5 is a schematic view showing a novel article for disposition about the ankle of a patient, wherein the novel article is configured to receive magnets which can be used to create a localized magnetic field in order to steer therapeutic USPIO nanoparticle-labeled cells to a therapy site within the body and/or to retain the therapeutic USPIO nanoparticle-labeled cells at that location over extended periods of time and/or while the patient is mobile.
Figure 6:
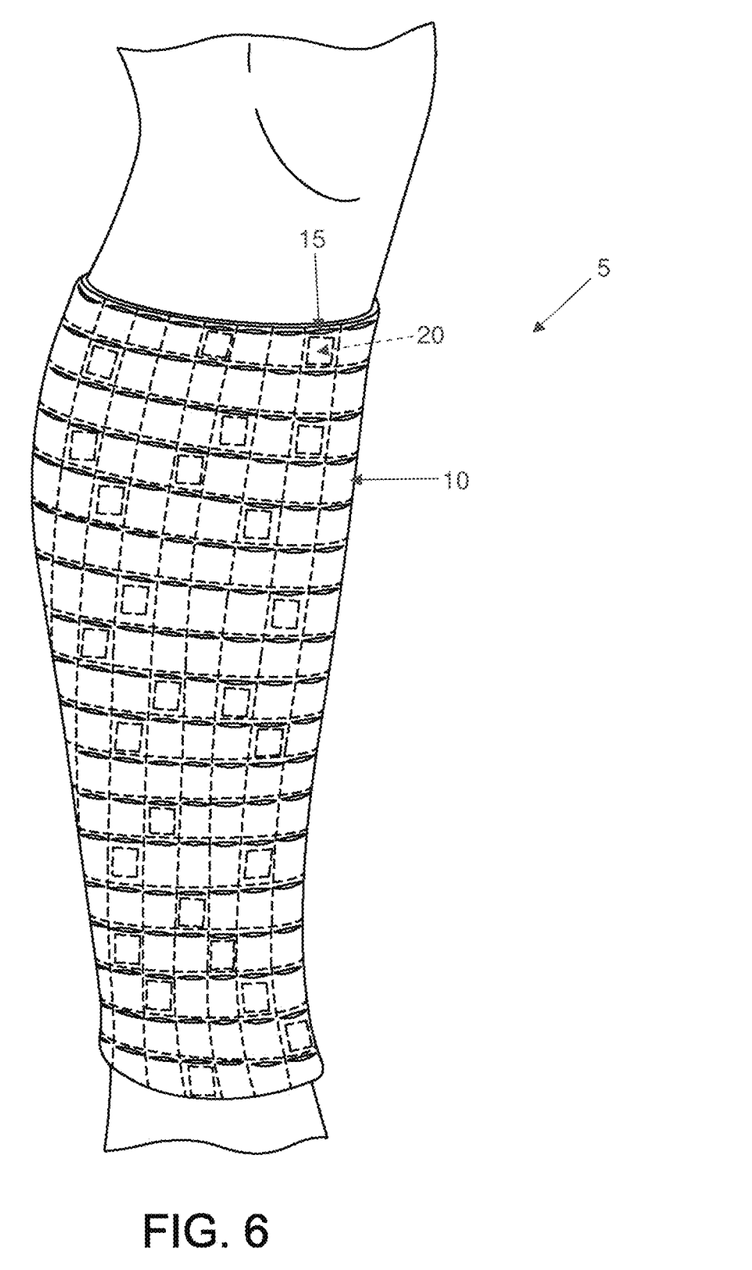
FIGS. 6-10 are schematic views showing a novel article for disposition about the calf of a patient, wherein the novel article is configured to receive magnets which can be used to create a localized magnetic field in order to steer therapeutic USPIO nanoparticle-labeled cells to a therapy site within the body and/or to retain the therapeutic USPIO nanoparticle-labeled cells at that location over extended periods of time and/or while the patient is mobile.
Figure 7:
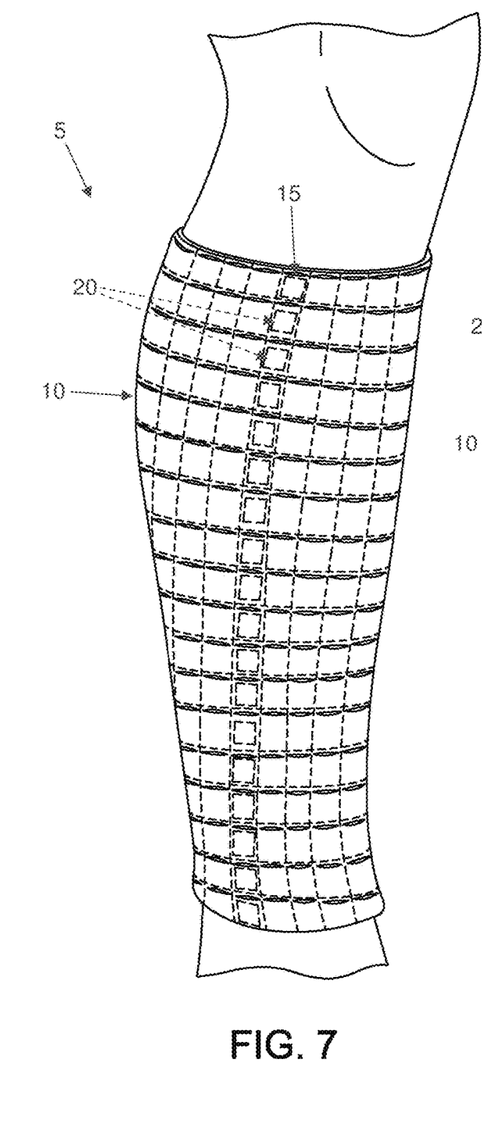
Figure 8:
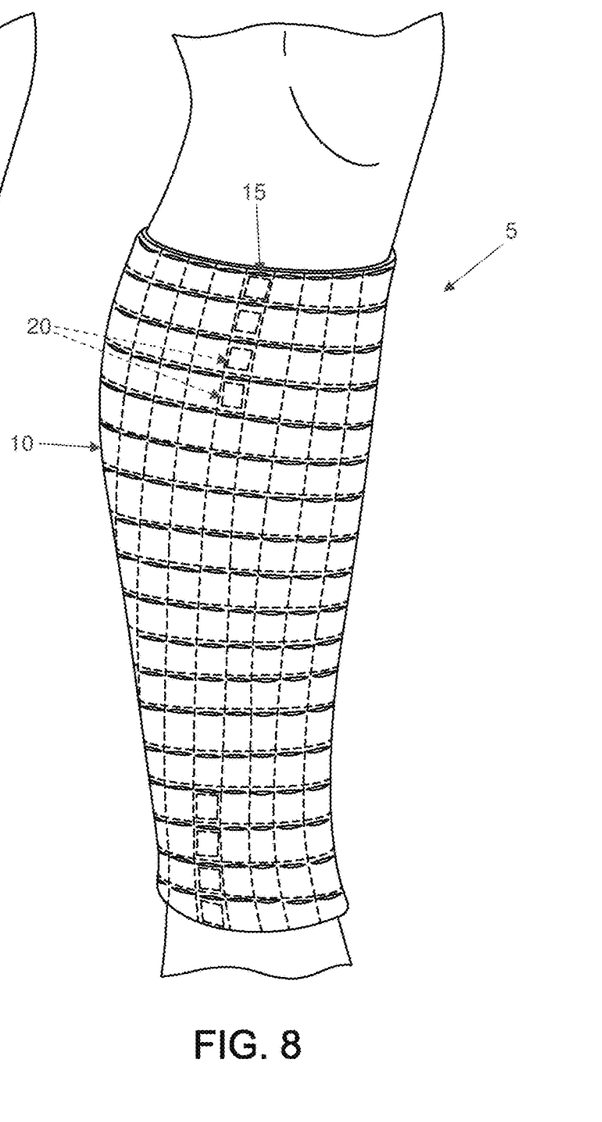
Figure 9:
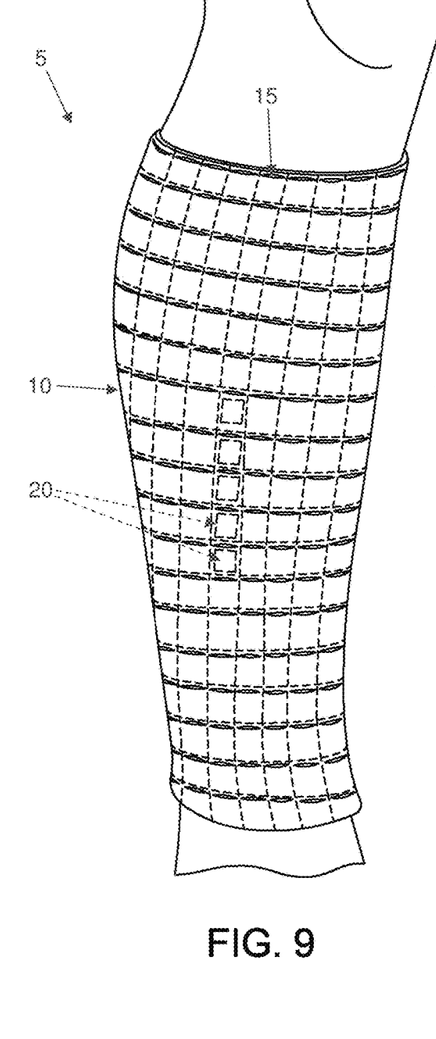
Figure 10:
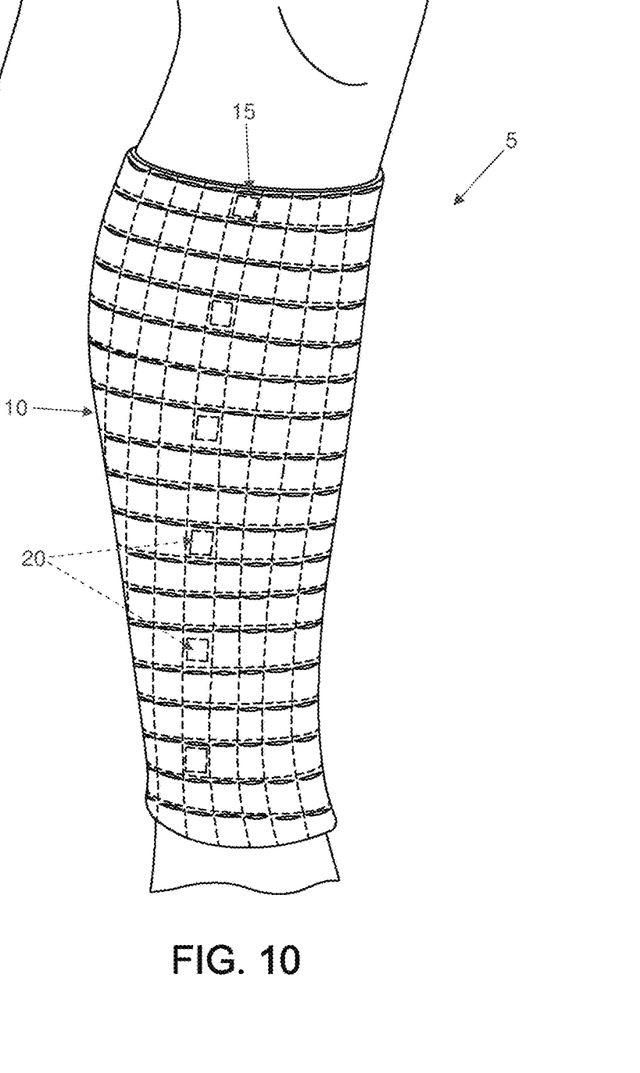

FIG. 5 shows an exemplary article (e.g., a sleeve, wrap, covering, brace, etc.) adapted to be worn on the ankle of a patient.

FIGS. 6-10 show an exemplary article (e.g., a sleeve, wrap, covering, brace, etc.) adapted to be worn on the calf of a patient. Note how magnets 20 are positioned with different dispositions in FIGS. 6-10, illustrating how the present invention provides the opportunity to position appropriate magnets 20 at appropriate locations about the calf of the patient.

It should be appreciated that, in addition to customizing the magnetic field provided about the target tissue by varying the locations of magnets 20 on article 5, it is also possible to tailor the magnetic field by controlling the orientation of magnets 20 provided on article 5. By way of example but not limitation, magnets 20 may be arranged relative to one another such that their individual magnetic fields form a composite magnetic field having the desired properties. In one form of the invention, magnets 20 may be disposed in pockets 15 such that they comprise a Halbach array, thereby generating an augmented magnetic field on one side of the magnet array while canceling the magnetic field to zero (or near zero) on the other side of the magnet array. In another form of the invention, magnets 20 may be disposed in pockets 15 such that they comprise a Halbach cylinder, thereby generating an augmented magnetic field within the cylinder while canceling the magnetic field to zero (or near zero) outside the cylinder.

Additionally, it should be appreciated that the ultra-small superparamagnetic iron oxide (USPIO) nanoparticles (and hence, the USPIO nanoparticle-containing cells) can be visualized using imaging such as MRI (e.g., with the USPIO nanoparticles acting as a contrast agent, image enhancer, etc.). Therefore, after the USPIO nanoparticle-containing cells have been injected into the body, their locations can be visualized and potentially tracked via MRI. Significantly, the magnetic fields provided by novel article 5 (e.g., sleeve, wrap, covering, brace, etc.) can be customized "on the fly" by observing (by MRI imaging) the location of the USPIO nanoparticle-containing cells, e.g., by adding (or removing) magnets 20 to (or from) appropriate pockets 15 (or other enclosures) so as to tailor the magnetic field and thereby help maximize the location of the injected therapies based on the information obtained through imaging, i.e., to further direct the USPIO nanoparticle-containing cells to the target tissue and/or to maintain the USPIO nanoparticle-containing cells at the target tissue. Article 5 (e.g., sleeve, wrap, covering, brace, etc.) is, therefore, preferably constructed so as to allow for adjustments in its associated magnetic fields in order to optimize the location of the injected therapies based on the information provided by imaging of the USPIO nanoparticle-containing cells in vivo.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for directing therapeutic ultra-small superparamagnetic iron oxide (USPIO) nanoparticle-labeled cells to selected locations within the body of a patient and/or for retaining therapeutic ultra-small superparamagnetic iron oxide (USPIO) nanoparticle-labeled cells at selected locations within the body of the patient, the method comprising:

providing an article comprising a body of material configured to be secured about the body of a patient and having a plurality of pockets thereon, wherein each pocket is sized to receive and retain one or more magnets therein, and wherein each pocket comprises an opening along a side of the pocket for permitting the one or more magnets to be selectively added to, or removed from, the pocket;

injecting therapeutic ultra-small superparamagnetic iron oxide (USPIO) nanoparticle-labeled cells into a target therapy site within the body of the patient;

securing the article to the body of the patient;

inserting at least two magnets into at least two pockets of the plurality of pockets through the openings of the at least two pockets such that the at least two magnets together generate a tailored magnetic field, with the at least two magnets being inserted into the at least two pockets of the plurality of pockets so that the tailored magnetic field directs the therapeutic ultra-small superparamagnetic iron oxide (USPIO) nanoparticle-labeled cells to the target therapy site and/or retains the therapeutic ultra-small superparamagnetic iron oxide (USPIO) nanoparticle-labeled cells at the target therapy site; and adjusting the tailored magnetic field so as to further direct the therapeutic ultra-small superparamagnetic iron oxide (USPIO) nanoparticle-labeled cells to the target therapy site and/or so as to further retain the therapeutic ultra-small superparamagnetic iron oxide (USPIO) nanoparticle-labeled cells at the target therapy site, wherein the tailored magnetic field is adjusted by at least one of (i) removing at least one of the at least two magnets through the opening of the plurality of pockets, (ii) moving at least one of the at least two magnets out through the opening in one of the plurality of pockets and in through the opening in a second one of the plurality of pockets, and (iii) inserting a magnet through the opening of one of the plurality of pockets.

2. A method according to claim 1 wherein MRI visualization is used to observe the position of the therapeutic USPIO nanoparticle-labeled cells relative to the target therapy site.

3. A method according to claim 1 wherein the article comprises a sleeve for making a gripping fit about the body of the patient.

4. A method according to claim 1 wherein the article comprises a wrap for securement about the body of the patient.

5. A method according to claim 1 wherein the article comprises a brace for securement about the body of the patient.

6. A method according to claim 1 wherein each pocket is rectangular.

7. A method according to claim 1 wherein each pocket is non-rectangular.

8. A method according to claim 1 wherein at least one opening of the plurality of pockets comprises a hook and loop closure mechanism for closing the opening.

9. A method according to claim 1 wherein the plurality of pockets are all the same shape.

10. A method according to claim 1 wherein the plurality of pockets comprises a variety of shapes.

11. A method according to claim 1 wherein the magnets are all the same size.

12. A method according to claim 1 wherein the magnets are a mix of different sizes.

\* \* \* \* \*